United States Patent [19]

Praxl et al.

[11] 4,213,967
[45] Jul. 22, 1980

[54] PESTICIDE CONTAINING IGNITION INHIBITOR

[75] Inventors: Werner Praxl, Rimbach; Reiner Ehret, Weinheim, both of Fed. Rep. of Germany

[73] Assignee: Dr. Werner Freyberg, Chemische Fabrik Delitia Nachf., Laudenbach/Bergstr, Fed. Rep. of Germany

[21] Appl. No.: 919,176

[22] Filed: Jun. 26, 1978

[30] Foreign Application Priority Data

Jul. 1, 1977 [DE] Fed. Rep. of Germany ....... 2729887

[51] Int. Cl.$^2$ ............................................. A01N 11/00
[52] U.S. Cl. .................................................... 424/128
[58] Field of Search ......................................... 424/128

[56] References Cited

U.S. PATENT DOCUMENTS

| 2,719,751 | 3/1973 | Rauscher et al. | 424/128 |
| 2,826,486 | 3/1958 | Hüter | 424/128 |
| 2,826,527 | 3/1958 | Hüter | 424/128 |
| 3,132,067 | 5/1964 | Rauscher et al. | 424/128 |
| 3,159,536 | 12/1964 | Marotta | 424/128 |
| 3,624,198 | 11/1971 | Arbaugh | 424/128 |
| 3,917,823 | 11/1975 | Kapp | 424/128 |
| 4,013,790 | 3/1977 | Kapp | 424/128 |

OTHER PUBLICATIONS

Wazer; Phosphorus and Its Compounds, vol. 1 (1958).

*Primary Examiner*—Allen J. Robinson
*Attorney, Agent, or Firm*—Thomas V. Michaelis; Joseph P. Nigon

[57] ABSTRACT

The invention provides a pesticide containing an aluminium or magnesium phosphide and an ignition inhibiting agent essentially consisting of at least one aromatic hydrocarbon which suppresses the tendency of phosphin evolved under the influence of e.g. atmospheric moisture, to self-ignite.

4 Claims, No Drawings

PESTICIDE CONTAINING IGNITION INHIBITOR

BACKGROUND OF THE INVENTION

In the fight against stock pests such as insects and rodents, there are used today, on a very considerable scale, agents which on exposure to moisture from the atmosphere or from grain, evolve highly active phosphin. Agents containing alkaline earth or earth metal phosphides have been recognized as being particularly suitable; phosphides of calcium, magnesium and aluminum have been found to be particularly advantageous.

Phosphin, however, tends to self-ignite, and this characteristic requires special precautions for ensuring substantially complete safety in the use of these agents. Up to now attempts were made to meet this requirement by control of the velocity of formation of the phosphin and/or suppression of its tendency to self-ignite.

These attempts pursued a variety of approaches. Thus it is known to use phosphide containing pesticides in special water-tight packages which, however, are permeable to gas and moisture. In practice, however, this proposal has proven effective only in certain special fields of application.

Other methods which have been suggested, operate by rendering phosphide particles, or groups of such particles, hydrophobic by means of water-repellent substances. Among the materials contemplated for this purpose are paraffins, waxes, stearates, silicones and artificial resins. Another known method involves the embedding of the phosphides in plastics.

The afore-mentioned procedures are designed to impede, by control of the velocity of formation of phosphin, the generation of phosphin-air mixtures with their tendency to self-ignite. If in accordance with these known methods, the phosphide is present in hydrophobic form, there is indeed an influence on hydrolysis, but an adequate protection against self-ignition of the phosphin generated is not ensured in this manner.

Also known is a proposal to suppress the tendency of phosphin to self-ignite, by the addition of thermally readily decomposable substances. Preferred among the substances employed for this purpose, are those which split off $CO_2$, and partly $NH_3$, such as sodium carbonate, sodium bicarbonate, ammonium carbonate, ammonium bicarbonate, and in particular ammonium carbaminate. It is also known to admix to the phosphides, certain readily volatile organic substances the latent heat of which surrounds the phosphide particles with a cold zone designed to prevent that heat accumulation apt to trigger the auto-ignition of the phosphin.

A reliable protection from self-ignition of the phosphin, and the assurance of safety in the handling of the phosphide, however, is not accomplished in this manner. It is in the nature of a thermally readily decomposable or readily volatile substance that its effective life is limited; this is particularly true if the phosphide to be protected in this manner, is to be used at relatively elevated temperatures. Inasmuch as the formation of hydrogen phosphide, or phosphin, is an exothermic process, such a rise in temperature may occur even in areas having a moderate climate.

A relatively recent publication recommends the addition to the phosphides, of oxygen or nitrogen containing organic substances which are supposed to inhibit the auto-ignition of the phosphin. Tests have demonstrated, however, that the inhibitors recommended fail to be effective to an acceptable degree. Moreover, not a small part of the substances recommended are quite unsuitable for toxicological reasons, while others are far from being readily available.

BRIEF SUMMARY OF THE INVENTION

It is the principal aim of the invention to provide phosphide containing pesticides which are quite safe even if used under difficult conditions, and particularly under difficult climatic conditions, and which avoid the safety hazards caused by climatic or other problems encountered in the prior art. The invention accomplishes this objective by providing a pesticide containing an aluminium or magnesium phosphide and comprising, in addition, an ignition inhibiting agent essentially consisting of at least one aromatic hydrocarbon.

In accordance with a preferred emodiment of the invention, the aromatic hydrocarbon(s) selected to act as ignition inhibitors should be liquid, and have a boiling point between about 130° and about 180° C.

DETAILED DESCRIPTION OF THE INVENTION

The ignition inhibiting agents according to the invention may be exemplified by substituted benzene or naphthalene compounds. Preferably, the substituents are saturated, possibly branched alkyl rests with from 1 to 4, and preferably from 1 to 3 carbon atoms.

In the case of a benzene nucleus, preferably up to 5 alkyl substituents may be present, while with a naphthalene nucleus, the presence of up to 3 alkyl substituents is preferred.

Alkyl substituents contemplated by the invention include the methyl, ethyl, n-propyl, i-propyl, n-butyl and i-butyl rests, insofar as saturated hydrocarbon groups are concerned.

Compounds contemplated by the invention having unsaturated substituents are, for example, the following: styrene, propenylbenzene, ethylbenzene, i-propenylbenzene, methylstyrene, butenylbenzene, methylpropenylbenzene, and trimethylstyrene.

Ignition inhibiting additives preferred according to the invention include, for example, mesitylene (1,3,5-trimethylbenzene), pseudo-cumene (1,3,4-trimethylbenzene), 1,3-diethylbenzene, and p-cymene (1-isopropyl-4-methylbenzene). All substances named, of course, may be used in pure form, or in the form of isomeric mixtures.

Preferably, the hydrocarbons contemplated by the invention are adsorptively bound to a carrier, for being admixed to the phosphides in a manner known by itself. As carrier materials the invention contemplates e.g. highly disperse silicic acids, molecular sieves, and aluminum oxides. They are inert and serve merely as deposit and control substances for the ignition inhibiting additive. It has been found that as a rule, an addition of 0.5 to 10 percent, and preferably from about 1 to about 5 percent by weight of the phosphide, is sufficient for the ignition inhibiting additive.

Once they are intimately mixed with the ignition inhibiting agents and other commonly used adjuvants, the phosphides are ready for use. They may also be used—possibly following the addition of auxiliary agents—in granulated form, or in the form of tablets. It is of interest to note in this connection that some of the ignition inhibiting agents contemplated by the invention, are capable of acting also as solvents for certain granulating agents. Auxiliary agents contemplated by the invention primarily include binders such as polyethyleneoxide with a molecular weight between about 4,000 and 20,000, polyvinylpyrrolidone, vinylpyrrolidone-containing water-soluble copolymers, alginates, dextrin, gelatin and cellulose ether.

The ignition inhibiting additives according to the invention, generally, present no toxicological problems; residue, therefore, is no problem either.

The ignition inhibiting additives according to the invention ensure the safe manufacture, storage and use of the phosphide containing pesticides. They eliminate any absolute requirement for the phosphides to be rendered hydrophobic, and the compositions according to the invention open up important new fields of application. This is particularly important under the aspect of gas evolution of short duration.

Also embraced by the invention is a method of producing the pesticides described above which comprises depositing the ignition inhibiting additive(s) on a preferably porous carrier substance, and mixing the same with the metal phosphides—which may or may not be rendered hydrophobic—and other adjuvants which may be desired.

In a preferred embodiment of the process of making a pesticide according to the invention, the mixture just mentioned is mixed with a binder, and granulated.

In order to test the effectiveness of the ignition inhibiting agents according to the invention, phosphide, ignition inhibiting agent adsorbed on a carrier, urea as a pressing aid, and in some instances, an agent for rendering the substances hydrophobic, were thoroughly mixed and pressed into compacts; these compacts were then stored under varying conditions and exposed to the influence of atmospheric or grain moisture, or treated with (liquid) water. These tests demonstrated that the ignition inhibiting additives according to the invention were entirely effective in each and every test, whereas comparative tests omitting the ignition inhibiting agents of the invention, frequently incurred ignition. It is particularly noteworthy that the compacts or tablets which were protected by the ignition inhibiting additives according to the invention, did not ignite even under conditions of relatively long duration of gas evolution, followed by treatment with water.

The pesticides of the invention may be used as compacts or tablets, in bags, tapes or strips, in a manner known in the art.

The following examples are intended to illustrate the invention, but are not intended to limit the invention in any way.

EXAMPLE 1

70 parts by weight of commercial aluminum phosphide were rendered hydrophobic by admixture of 4 parts of hard paraffin. To 74 parts of this hydrophobic phosphide were added 2 parts of 1-methyl-4-isopropylbenzene adsorptively bound to 1 part of highly disperse silicic acid, and 23 parts of urea, and the whole was thoroughly mixed.

The composition thus obtained was formed into tablets of 3 g each.

EXAMPLE 2

74 parts by weight of the hydrophobic phosphide prepared in accordance with Example 1, were added to 20 parts of urea, and 6 parts of a mixture of 1,3,5-trimethylbenzene and highly disperse silicic acid in a ratio of 4:2. The resulting combination of all components was thoroughly mixed and pressed into tablets with a diameter of 18 mm and weighing 3 g each.

EXAMPLE 3

70 parts by weight of commercial magnesium phosphide, 15 parts of urea, and 10 parts of ammonium stearate were thoroughly mixed with 5 parts by weight of a mixture of 1,2,4-trimethylbenzene and highly disperse silicic acid in a ratio of 4:2; the resulting mixture was compressed into tablets of 3 g each.

EXAMPLE 4

70 parts by weight of commercial aluminum phosphide, 24 parts of urea, and 3 parts of 1,3,5-trimethylbenzene were thoroughly mixed and granulated with the aid of 30 parts by weight of a 10% solution of PVP (polyvinylpyrrolidone) in $CH_2Cl_2$.

In order to verify the efficacy of the ignition inhibiting agents according to the invention, the compositions of the foregoing examples were subjected to a series of tests, as follows.

Test 1

140 parts by weight of commercial aluminum phosphide were rendered hydrophobic by admixture of 8 parts of hard paraffin. To 74 parts of this hydrophobic phosphide were added 2 parts of 1-methyl-4-isopropylbenzene adsorptively bound to 1 part of highly disperse silicic acid, and 23 parts of urea, the whole being thoroughly mixed.

The remaining 74 parts of the hydrophobic phosphide received an addition of 26 parts of urea only, this combination then being thoroughly mixed.

The two compositions were formed into tablets of 3 g each.

The two kinds of tablets were subjected to the following two tests:

A. 10 tablets from each series were placed in a 400 ml beaker, and 5 ml of water were added. After a short time, the phosphin evolved from the tablets containing no ignition inhibiting agent according to the invention, ignited, whereas no ignition occurred with the tablets containing the ignition inhibitor of the invention.

B. In the other test, 20 tablets from each of the two categories were inserted into tubular tablet containers which were then tightly closed. The containers were stored at 70° C. Following a storage period of one day, ignition occurred in the container with the tablets including no ignition inhibitor; no ignition, however, was encountered in the other container with the tablets incorporating the ignition inhibiting agent according to the invention.

Test 2

74 parts by weight of the phosphide—rendered hydrophobic— of Example 1, were added to 20 parts of urea, and 6 parts of a mixture of 1,3,5-trimethylbenzene and highly disperse silicic acid in a ratio of 4:2. The resulting combination of all components was thoroughly mixed and pressed into tablets having a diameter of 18 mm and weighing 3 g each.

These tablets were compared with a composition available on the market in the form of tablets of similar dimension and identical weight; this composition essentially consists of aluminum phosphide, ammonium carbonate, and paraffin.

Batches of 10 tablets of each of the two afore-mentioned compositions were placed in 250 ml beakers and left standing for 3 hours at 30° C. to permit gas to evolve. Following the 3 hours' waiting period, 15 ml of water were added in each beaker. This test was conducted three times. While with the tablets containing the ignition inhibiting agent of the invention, no self-ignition occurred in any of the three instances, the tablets lacking the present ignition inhibitor failed to prevent ignition in two out of three tests.

Test 3

70 parts by weight of commercial magnesium phosphide, 15 parts of urea, and 10 parts of ammonium stearate were thoroughly mixed with a mixture, in a 4:2 ratio, of 1,2,4-trimethylbenzene and highly disperse silicic acid. The resulting mixture was compressed into tablets of 3 g each.

For the sake of comparison, corresponding tablets were prepared which lacked the ignition inhibiting agent according to the invention. They were composed of 70 parts of magnesium phosphide, 30 parts of urea and 10 parts of ammonium stearate.

10 tablets of each composition were placed in 400 ml beakers, and 30 ml of water were poured over the contents of each beaker. After a short while, a violent ignition occurred in the beaker containing the tablets lacking the ignition inhibitor of the invention, but no ignition was encountered in the other beaker with the tablets containing the present ignition inhibiting agent.

Test 4

Following the procedure described in Example 4, 70 parts by weight of commercial aluminum phosphide, 24 parts of urea, and 3 parts of 1,3,5-trimethylbenzene were thoroughly mixed, and granulated with the aid of 30 parts by weight of a 10% solution of polyvinylpyrrolidone in $CH_2Cl_2$.

The granulate obtained on evaporation of the solvent, in one test, was treated with water, and in another test, was left standing to be exposed to the hydrolytic influence of moisture from the ambient air.

No ignition was observed in either test; evidently, the phosphin evolved in both tests, was effectively prevented from self-ignition under the influence of water or atmospheric moisture, by the presence in the granulate, of the ignition inhibiting agent according to the invention.

Following the gas evolution, the residue of the granulate may be thoroughly moistened with water, and removed.

In order to further explore and explain the invention, still other compositions were prepared and tested which are exemplified in the following additional examples.

Example 5

70 parts by weight of commercial aluminum phosphide and 3 parts of stearic acid were heated to 100° C. and thoroughly mixed under exclusion of air. The mixture was permitted to cool to room temperature, and then mixed with 20 parts of urea, and 7 parts of a mixture, in a 3:2 ratio, of p-isopropyltoluene with highly disperse silicic acid. The resulting composition was compressed into tablets of 3 g each.

10 of these tablets were subjected to the testing procedure described above under the heading "Test 3". The present tablets containing an ignition inhibitor according to the invention, did not ignite.

Example 6

Example 1 was repeated except that for the ignition inhibitor used therein, to wit: 1-methyl-4-isopropylbenzene, 1,3,5-trimethyl-2-propylbenzene was substituted.

The resulting composition, when pressed into tablets and contacted with water, failed to ignite, thus demonstrating the loss of any tendency on the part of the phosphin evolved, to self-ignite.

EXAMPLE 7

100 parts by weight of aluminum phosphide obtained from the elements by thermal reaction, were mixed with 2 parts of a reactive hydrogenpolysiloxane. The resulting hydrophobic phosphide was mixed with 88 parts of urea and 6 parts of 1,2,6-trimethylnaphthalene adsorptively bound to 4 parts of a molecular sieve 4 A. The whole was pelleted into compacts of 0.6 g. each. These compacts were filled into bottles which were hermetically sealed and subjected to a storage test according to the procedure described above under the heading "Test 1", part B.

The result was positive, i.e. no self-ignition occurred.

EXAMPLE 8

Batches of 40 g each of a granulate prepared in accordance with Example 4, were packed into small paper bags permeable to air and moisture. Three of these bags were placed in a bowl, and 250 ml of water were poured over them. No ignition occurred, thus demonstrating that the phosphin evolved was protected from self-ignition.

EXAMPLE 9

70 parts by weight of commercial aluminum phosphide, 20 parts of urea, 5 parts of aluminum stearate, and 5 parts of a 3:2 mixture of 1,2-dimethyl-4-propylbenzene and highly disperse silicic acid were thoroughly mixed and formed into tablets. Hydrogen phosphide evolved from these tablets did not ignite.

EXAMPLE 10

Example 9 was repeated except that the ignition inhibitor used therein, was replaced by a corresponding amount of a commercial isomeric mixture of dimethylbenzenes (about 20 percent of o-, 20 percent of p-, 60 percent of m-isomers; d=0.86; boiling point range between 135° and 140° C.)

The result was the same as in Example 9; no ignition occurred as evidently, the tendency to self-ignite of the phosphin evolved had been suppressed by the ignition inhibiting agent according to the invention.

We wish it to be understood that we do not desire to be limited to the exact details of composition or procedure described and exemplified herein, as modifications within the scope of the following claims may readily occur to those skilled in the art.

We claim:

1. A pesticide composition containing from about 40 to about 80 percent by weight of a metal phosphide selected from the group consisting of aluminum and magnesium phosphide, from about 15 to about 55 percent by weight of a pelleting agent, and as an ignition inhibiting agent, from about 0.5 to about 10 percent by weight, calculated on the metal phosphide, of a liquid aromatic hydrocarbon having a boiling point between about 130° and about 180° C. selected from the group consisting of hydrocarbons having a benzene or naphthalene nucleus and being substituted with alkyl substituents having from 1 to 4 carbon atoms, compounds with a benzene nucleus having up to 5 alkyl substituents, compounds with a naphthalene nucleus having up to 3 alkyl substituents, or isomeric mixtures of such aromatic hydrocarbons.

2. A pesticide composition according to claim 1, containing a carrier substance, said aromatic hydrocarbon being adsorptively bound to said carrier substance, the weight ratio of aromatic hydrocarbon to carrier substance being between about 3:1 and 1:3.

3. A pesticide composition according to claim 2, containing agents for rendering the metal phosphide hydrophobic, and binders.

4. A pesticide composition according to claim 2, in the form of tablets, tapes, strips or granulated materials.

* * * * *